United States Patent
Van Ommen

(10) Patent No.: US 10,245,233 B2
(45) Date of Patent: Apr. 2, 2019

(54) CONTROLLED RELEASE FROM PARTICLES ENCAPSULATED BY MOLECULAR LAYER DEPOSITION

(71) Applicant: Technische Universiteit Delft, Delft (NL)

(72) Inventor: Jan Rudolf Van Ommen, Delft (NL)

(73) Assignee: Technische Universiteit Delft, Delft (NL)

( * ) Notice: Subject to any disclaimer, the term of this patent is extended or adjusted under 35 U.S.C. 154(b) by 32 days.

(21) Appl. No.: 15/552,122

(22) PCT Filed: Feb. 25, 2016

(86) PCT No.: PCT/EP2016/054030
§ 371 (c)(1),
(2) Date: Aug. 18, 2017

(87) PCT Pub. No.: WO2016/135267
PCT Pub. Date: Sep. 1, 2016

(65) Prior Publication Data
US 2017/0367986 A1 Dec. 28, 2017

(30) Foreign Application Priority Data
Feb. 25, 2015 (NL) ..................... 2014348

(51) Int. Cl.
| | | |
|---|---|---|
| *A61K 9/50* | (2006.01) | |
| *B01J 8/24* | (2006.01) | |
| *B01J 8/18* | (2006.01) | |
| *B05D 1/22* | (2006.01) | |
| *B01J 8/40* | (2006.01) | |

(52) U.S. Cl.
CPC .......... *A61K 9/5073* (2013.01); *A61K 9/5031* (2013.01); *A61K 9/5089* (2013.01); *B01J 8/1827* (2013.01); *B01J 8/24* (2013.01); *B01J 8/40* (2013.01); *B05D 1/22* (2013.01); *B01J 2208/00938* (2013.01)

(58) Field of Classification Search
None
See application file for complete search history.

(56) References Cited

U.S. PATENT DOCUMENTS

| | | |
|---|---|---|
| 8,118,243 B2 | 2/2012 | Pfeffer et al. |
| 2009/0162429 A1 | 6/2009 | Berthoumieu et al. |
| 2012/0009343 A1 | 1/2012 | Van Ommen |
| 2013/0084312 A1 | 4/2013 | Caputo et al. |
| 2013/0254854 A1 | 9/2013 | Moganti et al. |

FOREIGN PATENT DOCUMENTS

| | | |
|---|---|---|
| WO | WO-2008/069894 A2 | 6/2008 |
| WO | WO-2009/091384 A1 | 7/2009 |
| WO | WO-2014/044907 A1 | 3/2014 |
| WO | WO-2014/147541 A2 | 9/2014 |

OTHER PUBLICATIONS

Arkels et al., "Cyclic azasilanes: volatile coupling agents for nanotechnology", Silanes and Other Coupling Agents, 2004, vol. 3, pp. 179-191.
Beetstra et al., "Atmospheric pressure process for coating particles using atomic layer deposition", Chemical Vapor Deposition, 2009, vol. 15, pp. 227-233.
Chen et al., "Nanoporous nitrogen-doped titanium dioxide with excellent photocatalytic activity under visible light irradiation produced by molecular layer deposition", Angewandte Chemie International Edition, 2013, vol. 52, No. 35, pp. 9196-9200.
George et al., "Molecular layer deposition of organic and hybrid organic-inorganic polymers", Material Matters, 2008, vol. 3.2, 6 pgs.
Kwak et al., "Colored and luminous aliphatic polyester via one-pot intra- and intermolecular knoevenagel reactions", Macromolecules, 2004, vol. 37, pp. 2021-2025.
Sundberg et al., "Organic and inorganic-organic thin film structures by molecular layer deposition: A review", Beilstein Journal of Nanotechnology, 2014, vol. 5, pp. 1104-1135.
International Search Report issued in International Patent Application No. PCT/EP2016/054030, dated Jun. 2, 2016.

*Primary Examiner* — Jeffrey T. Palenik
(74) *Attorney, Agent, or Firm* — Foley & Lardner LLP

(57) ABSTRACT

The invention provides a slow-release material comprising particles, wherein the particles comprise a core comprising an active component and a multilayer shell, wherein the multi-layer shell comprises a molecular layer deposition (MLD) multi-layer, wherein the active component comprises one or more of a pharmaceutical compound and a nutraceutical compound, for use in the treatment of a disease.

20 Claims, 6 Drawing Sheets

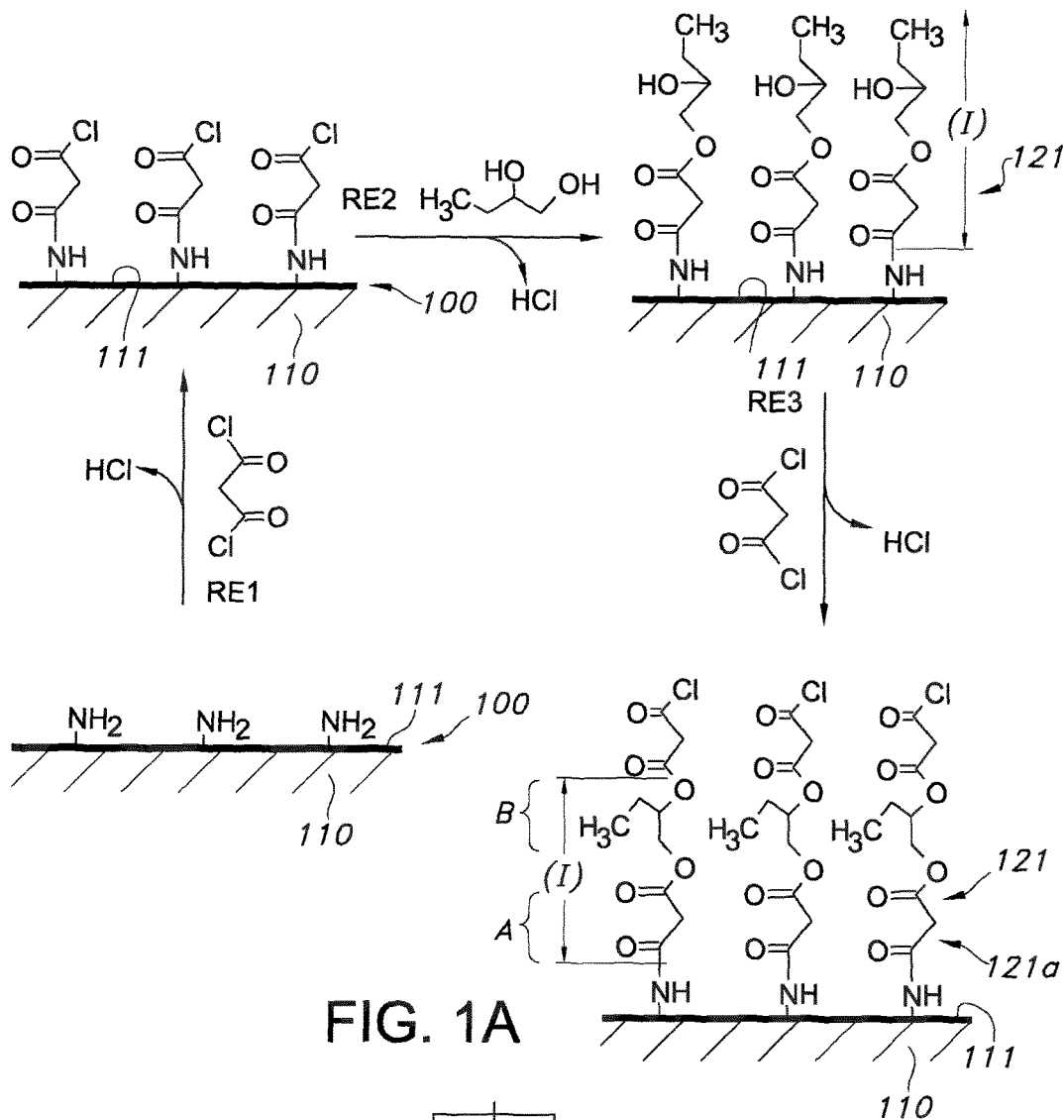
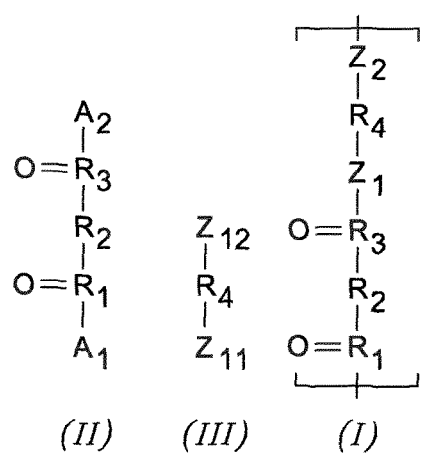
FIG. 1A
FIG. 1B

CONTROLLED RELEASE FROM PARTICLES ENCAPSULATED BY MOLECULAR LAYER DEPOSITION

CROSS-REFERENCE TO RELATED APPLICATIONS

This application is the National Phase of International Patent Application No. PCT/EP2016/054030, filed Feb. 25, 2016, published on Sep. 1, 2016 as WO 2016/135267 A1, which claims priority to Netherlands Patent Application No. 2014348, filed Feb. 25, 2015. The contents of these applications are herein incorporated by reference in their entirety.

FIELD OF THE INVENTION

The invention relates to a (particulate) slow-release material, especially for e.g. the treatment of a disease. The invention also relates to a method for the production of such (particulate) slow-release material. The invention also relates to an apparatus for the production of the (particulate) slow-release material.

BACKGROUND OF THE INVENTION

Slow release of active components, such as pharmaceuticals, is known in the art. US2009162429, for instance, describes a pharmaceutical or nutraceutical composition with sustained release of an active ingredient comprising at least one coated granule; the coated granule being composed of a particle that comprises said active ingredient and is coated with at least two coatings that comprise a combination of excipients. US2009162429 also describes a process for the preparation of the composition. US2009162429 describes amongst others a pharmaceutical or nutraceutical composition comprising at least one coated granule providing sustained release of an active ingredient, the coated granule being composed of a particle that comprises the active ingredient and is coated with at least two coatings, wherein the coatings comprise a combination of excipients of: (i) at least one copolymer (a) of esters of acrylic acid and of methacrylic acid having a molar percentage of quaternary ammonium groups of less than or equal to 8%; (ii) a second copolymer (b) of esters of acrylic acid and of methacrylic acid having a molar percentage of quaternary ammonium groups of greater than 8%; wherein a ratio by weight of (a)/(b) is from 60/40 to 80/20, and wherein an amount of (a) is from 2.5% to 5.0% by dry weight based on the total weight of the composition.

Chaoqiu Chen et al., describe in Angew. Chem. Int. Ed. 2013, 52, p. 9196-9200, nanoporous nitrogen-doped titanium dioxide with excellent photocatalytic activity under visible light irradiation produced by molecular layer deposition. They claim to demonstrate a novel MLD process for preparing nanoporous N-doped $TiO_2$ films. The process is based on a four-step ABCB reaction sequence using $TiCl_4$ (precursor A), ethanolamine (precursor B), malonyl chloride (precursor C).

US2013/0084312 describes biocompatible polymeric nanoparticles for delivery of bioactive agents, and methods for preparing the particles. Polyoxalate nanoparticles of the subject technology show desired particle sizes suitable for use in drug delivery and a substantially uniform or narrow particle size distribution. The polyoxalate nanoparticles can contain water-soluble, poorly water-soluble, or water-insoluble drugs. The nanoparticles are nontoxic and are generally safe for use in humans. After being administered into the body, the nanoparticles with a high content of a bioactive agent entrapped therein can safely deliver the agent to target sites and stably release the drug at a controlled rate.

Renske Beetstra et al., describe in Chem. Vap. Deposition 2009, 15, p. 227-233, an atmospheric pressure process for coating particles using atomic layer deposition.

Giseop Kwak et al., describe in Macromolecules 2004, 37, p. 2021-2025 colored and luminous aliphatic polyester via one-pot intra- and intermolecular Knoevenagel reactions. It is described that an aliphatic polyester containing a malonate group in the main chain was prepared by a one-pot reaction of malonyl dichloride with ethylene glycol in the presence of trimethylamine.

SUMMARY OF THE INVENTION

In the last two decades, much effort has been put in towards the development of drug delivery systems which overcome the shortcomings of the traditional methods such as toxic effects due to unpredictable concentration levels, degradation of drugs in digestive tract before entering the bloodstream, non-personalized nature etc. With this development, proteins and peptides have become the natural choice for drugs due to their incredible specificity and bioactivity. However, their administration has been mostly limited to parental route due to their low bioavailability. Encapsulation of the active pharmaceutical component inside a shell is an attractive way to control the temporal and spatial release, by either varying the thickness or composition of the coating. To this end, a number of novel and efficient drug delivery systems have been developed based on encapsulation methods. However, a number of prior art solutions suffer from problems such as reliability, control of layer thickness, etc., which may have undesired effects when e.g. pharmaceuticals have to be delivered in a controlled way to a person.

Hence, it is an aspect of the invention to provide an alternative material, which preferably further at least partly obviates one or more of above-described drawbacks. Further, it is an aspect of the invention to provide a method for the production of such alternative material, which preferably further at least partly obviates one or more of above-described drawbacks. Yet, it is also an aspect of the invention to provide an alternative apparatus for the production of such material, which preferably further at least partly obviates one or more of above-described drawbacks.

Molecular layer deposition (MLD) was used to coat micron-sized protein particles in a fluidized bed reactor. Our results show that the dissolution rate of particles coated with MLD rapidly decreases with the increase in number of coating cycles, while the uncoated particles dissolve instantaneously.

MLD is a thin-film growth technique developed during the early 1990s for the deposition of molecular fragments on the surface of an active material, and has been an attractive method for the deposition of a variety of organic polymers and more recently hybrid organic-inorganic polymers. In a typical MLD process, molecular fragments of the bi-functional precursors are deposited on the surface of an active substrate. This process involves two different reactions: the first between the surface active group of the substrate and precursor-1; the other reaction is between precursor-1 and precursor-2. It is the self-terminating nature of these reactions which enables the deposition of ultra thin layers on the surface of the substrate. Herein, we show that controlled release of the active material can be achieved by MLD coating of active components (which can also be indicated as "active ingredients").

Hence, in a first aspect the invention provides (particulate) slow-release material comprising particles, wherein the particles comprise a core comprising an active component and a multi-layer shell, wherein the multi-layer shell comprises a molecular layer deposition (MLD) multi-layer, and wherein the active component especially comprises one or more components selected from the group of a pharmaceutical compound and a nutraceutical compound, especially (a pharmaceutical compound, even more especially a drug) for use in the treatment of a disease. It appears that with MLD the slow-release can easily be tuned, due to the fact that the MLD process can be used to completely control the number of layers that is deposited. In this way, substantially any realistic release time frame can be tuned. Further, it appears that with MLD good conformal layers can be made, substantially fully enclosing the cores. Nevertheless, it is herein not excluded that one or more layers may not be entirely conformal. In general however, notwithstanding the fact that individual layers may not be entirely conformal, with the present method the multi-layer shell will substantially entirely cover the surface of the core. Hence, the invention is easier to scale-up than alternative approaches (often liquid based), which makes it cheaper. Further, at the same time a higher precision can be reached than with competing methods. This may reduce undesired side effects e.g. when using the method for pharmaceutical purposes. Possible agglomeration problems—if any—of the present method can be circumvented as defined below. For certain applications, it will be attractive to have full control over the coating thickness at nm scale, while the coating is conformal. Such a method has a huge scope for extensibility to coating of bio-organic nanoparticles. With molecular layer deposition (MLD) such a precise and well-controlled coating appears to be achievable. Hence, in embodiments the invention uses fluidized bed MLD.

The cores, i.e. the basic particles, may include the active component. This may in embodiments refer to a core particle comprising the active component and one or more other components. In yet other embodiments the core particles substantially include only the active component. Often, however, the core may include a carrier and/or a filler, such as herein especially a pharmaceutically acceptable carrier and/or a pharmaceutically acceptable filler. Note that e.g. the terms "active component", "carrier", "filler", "pharmaceutical", etc., may also relate to "active components", "carriers", "fillers", "pharmaceuticals", etc., respectively.

Herein, the term "treatment" may relate to one or more of a therapeutic treatment and a prophylactic treatment.

The term "active component" may relate to one or more of a diagnostic marker, a nutraceutical, a drug, etc. Herein, the term "pharmaceutical" or "pharmaceutical compound" may refer to one or more of a drug (pharmaceutical drug or medicament), a diagnostic marker (such as for MRI), etc. The term "active component" may in an embodiment also refer to a bioactive compound, including a pesticide, a herbicide, a pheromone, etc. Therefore, especially the active component comprises one or more of a pharmaceutical compound and a nutraceutical compound. The term "nutraceutical" may amongst others refer to a nutrient, a dietary supplement, a herbal product, etc. The term nutraceutical may especially refer to a food product also having pharmaceutical function. Hence, the term "active component" may in embodiments refer to one or more of a drug and a dietary supplement. In yet a further specific embodiment, the active component comprises one or more of a drug and a pharmaceutical compound, especially at least a pharmaceutical compound. The active component may e.g. include a peptide and/or a protein, such as an enzyme.

Carriers and/or fillers may e.g. include one or more of a hydrophilic polymer, an excipient, a binder, a lubricant, an (other) edible material, an antioxidant, etc. etc., Examples thereof are known in the art, are amongst others described in WO2014147541, which is herein incorporated by reference, and non-exhaustively listed here below.

Suitable hydrophilic polymers include, but are not limited to, water swellable cellulose derivatives, polyalkylene glycols, thermoplastic polyalkylene oxides, acrylic polymers, hydrocolloids, clays, gelling starches, swelling cross-linked polymers, and mixtures thereof. Examples of suitable water swellable cellulose derivatives include, but are not limited to, sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols include, but are not limited to, polyethylene glycol. Examples of suitable thermoplastic polyalkylene oxides include, but are not limited to, poly(ethylene oxide). Examples of suitable acrylic polymers include, but are not limited to, potassium methacrylatedivinylbenzene copolymer, polymethyl-methacrylate (PMMA), high-molecular weight cross-linked acrylic acid homopolymers and copolymers such as those commercially available from Noveon Chemicals under the tradename CARBOPOL™. Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and mixtures thereof. Examples of suitable gelling starches include, but are not limited to, acid hydrolyzed starches, swelling starches such as sodium starch glyco late and derivatives thereof, and mixtures thereof. Examples of suitable swelling cross-linked polymers include, but are not limited to, cross-linked polyvinyl pyrrolidone, cross-linked agar, and cross-linked carboxymethylcellulose sodium, and mixtures thereof.

The carrier may contain one or more suitable excipients. Examples of suitable excipients include, but are not limited to, fillers, adsorbents, binders, disintegrants, lubricants, glidants, release-modifying excipients, superdisintegrants, antioxidants, and mixtures thereof.

Suitable binders include, but are not limited to, dry binders such as polyvinyl pyrrolidone and hydroxypropylmethylcellulose; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, and starches; and mixtures thereof. Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their salts, such as magnesium stearate and stearic acid, talc, glycerides waxes, and mixtures thereof. Suitable glidants include, but are not limited to, colloidal silicon dioxide. Suitable release-modifying excipients include, but are not limited to, insoluble edible materials, pH-dependent polymers, and mixtures thereof.

Suitable insoluble edible materials for use as release-modifying excipients include, but are not limited to, water-insoluble polymers and low-melting hydrophobic materials, copolymers thereof, and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers, copolymers thereof, and mixtures thereof. Suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their salts, and mixtures thereof. Examples of suitable fatty acid esters include, but are not limited to, sucrose fatty acid esters, mono-, di-, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate, and mixtures thereof. Examples of super disintegrants include, but are not limited to, croscarmellose sodium, sodium starch glycolate and cross-linked povidone (crospovidone). In one embodiment the core contains up to about 5% by weight of such super disintegrant.

Examples of antioxidants include, but are not limited to, tocopherols, ascorbic acid, sodium pyrosulfite, butylhydroxytoluene, butylated hydroxyanisole, edetic acid, and edetate salts, and mixtures thereof. Examples of preservatives include, but are not limited to, citric acid, tartaric acid, lactic acid, malic acid, acetic acid, benzoic acid, and sorbic acid, and mixtures thereof.

The particles are especially core-shell particles, wherein the shell especially comprises a multi-layer shell (substantially enclosing the core).

In a specific embodiment, the core may comprise a diameter selected from the range of 1 nm-2 mm, such as at least 5 nm. The shell may have a thickness of e.g. up to about 4 µm, such as ranging from about 0.5 nm, like at least about 1 nm, such as in the range of about 2 nm-4 µm.

The particle size selected from this range indicates especially a weight averaged particle size. For specific applications, the particle size (i.e. of the core-shell particles) may differ. For instance, for gastro intestinal (GI) applications the particle size may be in the range of 0.01-2 mm. For applications in e.g. the circulatory system the particles may be much smaller, such as e.g. in the range of below 50 nm, like in the range of 5-20 nm. For applications outside the human or animal body, e.g. for water treatment (such as with a bio-active compound), etc., the particle sizes will in general be in the range of about 0.1-2 mm, though other dimensions may also be possible, dependent upon the application (and/or further processing of the particulate material).

Further, in embodiments especially the multi-layer shell comprises in the range of 2-1000 layers. Especially, the multi-layer comprises at least four layers, such as at least six layers. Herein, a layer may especially relate to a structure that is self-repeating. Especially, a layer may be indicated as the molecular structure including one ester bond or one carboxamide bond. The multi-layer is especially a replicating multi-layer, i.e. (AB)(AB), etc., wherein in fact AB indicate a single layer (as they are the product of two self-terminating reactions in a single cycle). However, other options are also possible, including (AB)(AC), but also all kind of other variations. An advantage of the herein describe MLD method is that one may relatively easily tune the chemical composition that is provided to the particle in the reactor (see also below).

Hence, the multi-layer may include a stack of identical layers, wherein especially each layer (AB) is obtainable by the two self-terminating reactions as described above. However, the multi-layer may also include a stack of alternating layers, such as e.g. (AB)(CD)(AB)(CD), or (AB)(AD)(AB)(AD), or (AB)(CD)(EF)(AB)(CD)(EF) etc. etc. Yet, the multi-layer may (thus) also include a plurality of layers, wherein two or more layers have different chemical compositions. Hence, the invention also includes multiple layers of different nature.

Especially, a first molecular layer is covalently linked to a surface of the core. The core may include material e.g. comprising amine groups or hydroxyl (OH) groups, etc. For instance, the active component and/or one or more of the optional filler and the optional carrier may comprise such group. However, optionally the core may also include a first coating, configured to enable the deposition of the multi-layer. Such coating is not further discussed; even though such coating may be considered as a layer of the multi-layer, herein the term "multi-layer" is especially related to the multi-layer provided by molecular layer deposition.

In yet a further specific embodiment, each layer of the multi-layer shell comprises a group defined by formula (I):

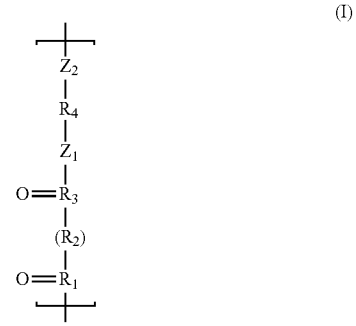

wherein $R_1$, $R_2$, $R_3$, and $R_4$ are independently selected from the group consisting of a carbon comprising group and a silicon comprising group, especially a carbon comprising group, wherein $Z_1$ and $Z_2$ are each independently selected from an oxygen or nitrogen comprising group, and wherein $R_2$ may optionally be present (therefore, $R_2$ is indicated as "$(R_2)$"). The (square) brackets indicate that the structure may be a repeating structure, but may also indicate that other molecular structures may be attached. For instance, the "lower" R1=O may be attached to a former hydroxyl or amine group of the core. The upper Z2 may e.g. be attached to yet a further group defined by formula I. The phrase "independently selected" in this context, but also in other contexts such as in relation to other groups, indicates e.g. that Z1 may be chosen independently of the choice of Z2. In principle, any Z1 and Z2 may be chosen even independently of the layer. In a specific embodiment, R1=R3=C, R2=CH$_2$, R4=-(CH$_2$)C(CH$_2$CH$_3$)—, and Z1=Z2=O. This would apply when malonyl chloride and 1,2-butanediol would have been applied (see further also below).

Though each layer of the multi-layer may be characterized by group I, the group I may differ from layer to layer, though in general a majority of the layers may have identical groups I. In such embodiments, block copolymer may be formed. Each layer may comprise a plurality of groups I.

As indicated above, R2 may be present or may not be present. In the case R2 is present, formula I is indicated as:

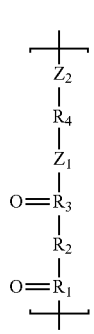

(I)

In other embodiments, R2 is not present, and formula I may be indicated as:

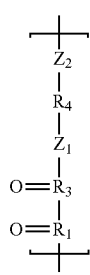

(I)

The invention may be of especially interest when the active component, optionally combined with one or more other materials in the cores, has a solubility that is larger than the solubility of the multi-layer shell. In this way, the release can be (better) controlled. In general, the solubility in aqueous media is relevant. Hence, in a specific embodiment the active component comprised by said core has active component solubility in water, wherein the multi-layer shell has a multi-layer shell solubility in water, and wherein the multi-layer shell solubility is smaller than the active component solubility.

An MLD cycle may consist of the following four steps: the first (organic) precursor is provided to the reactor and it reacts with the surface species, the excess precursor and possible byproducts are removed from the reactor, either by purging with inert gas such as nitrogen or argon, or by evacuation, the second (organic) precursor is provided to the reactor and it reacts with the surface species, and finally the excess precursor/possible byproducts are removed from the reactor. In an ideal case a monolayer is formed. To deposit thicker coatings this basic MLD cycle is repeated as many times as needed to reach the targeted coating thickness. An advantage of using a fluidized bed reactor is that in an easy way not reacted reactants can easily be removed. Another advantage is that highly conformal layers may be provided, since reactants can approach the particles from all sides. Further, an advantage is that in a continuous way the batch process of two partial layers can be executed in a continuous way. Hence, a multi-layer deposition scheme includes (at least) two reactants (or "precursors"), which are involved in two self-terminating reactions. Example of two suitable reactions are indicated below as compounds (II) and (III). Especially, the precursors II and III are organic molecules (without metal elements). However, the invention is not limited to MLD with only (purely) organic compounds. Optionally, also in one of the self-terminating reactions a metal organic compound or a metal halide compound may be applied.

Hence, in a further aspect the invention also provides a method for the production of a (particulate) slow-release material, especially as defined herein, the method comprising: (i) fluidizing particles (i.e. especially these particles are the later cores) comprising an active component in a reactor; (ii) applying molecular multi-layer deposition with self-terminating reactions on said fluidized particles in said reactor; and (iii) removing the thus obtained particles from said reactor, to provide said (particulate) slow-release material. Hence, especially a molecular deposition method is applied to generate a multi-layer ("molecular layer deposition multi-layer"). The multi-layer deposition will in general include for each layer that is generated a two stage process, wherein each stage is a self-terminating process. In between these process, the reactor may be purged to remove unreacted material. Herein, the term "molecular layer deposition multi-layer" especially refers to a multi-layer obtainable (or especially obtained) by molecular layer deposition (MLD).

With the present method, polymer chains may be grown with e.g. 2-1000 groups I in the respective polymer chains, In yet another aspect, the invention also provides a (continuous) process for depositing a coating onto particles being pneumatically transported in a tube, said process comprising: (i) providing a tube having an inlet opening and an outlet opening; (ii) feeding a carrier gas entraining particles into the tube at or near the inlet opening of the tube to create a particle flow through the tube; (iii) injecting a first reactant into the tube via an injection point downstream from the inlet opening of the tube for deposition on the surface of the particles in the particle flow in a self-terminating reaction; and (iv) injecting a second reactant into the tube via a further injection point downstream from the injection point of the first reactant for deposition on the surface of the particles in the particle flow in a self-terminating reaction, such as described in U.S. Ser. No. 13/254,854, (US2012/0009343) which is herein incorporated by reference. Hence, in this way, step by step the polymer chains may be grown.

It further appears in the present invention that introduction of further counter-agglomeration measures may be beneficial. Hence, in an embodiment during the molecular multi-layer deposition the reactor is subjected to a vibration having a frequency selected from the range of 1-200 Hz, such as 5-100 Hz. Especially, in yet another embodiment, the reactor may have a top part, wherein the method further includes providing a counter flow from the top part into the reactor. Especially, the counter flow is provided into the reactor via a micro jet. For instance, the micro jet may have an opening (nozzle) in the range of 50-500 μm. Also a plurality of micro jets may be applied, especially in the case of larger reactors. In a specific embodiment, the flow velocity of the fluidizing medium is in the range of about 0.001-20 m/s, such as 0.001-10 m/s, like especially 0.01-10 m/s (this may scale with the particle size). In yet a further specific embodiment, the gas flow through the micro jet may be in the range of 100-5000 m/s. Especially the combination of vibration and the counter flow appeared to provide good MLD coating results.

The molecular layer deposition process may be applied at different pressures, such as below or above atmospheric pressure. Further, the temperature of the reactor may be controlled, e.g. as function of the stability of the reactants. In a specific embodiment the molecular multi-layer deposition is executed at a temperature selected from the range of 20-250° C., such as in the range of 35-200° C., like in the range of 35-150° C. In further a specific embodiment the molecular multi-layer deposition is executed at a pressure selected from the range of 0.001-2 bar, such as in the range of 0.5-2 bar, like in the range of 0.8-2 bar, such as below, or at, or above atmospheric pressure. Good results in terms of high quality conformal layers were obtained. However, other conditions may (thus) also be possible.

To allow the molecules to covalently bind with the core (the particles), the particles may have at the outer surface ("surface") groups with which covalent bonds may be formed, such as amine groups and/or hydroxyl groups. Hence, in an embodiment the particles comprise a surface comprising amine groups. In another embodiment the particles comprise a surface comprising OH groups. In yet a further embodiment, the method comprises functionalizing the surface with one or more of an amine group and a hydroxyl group.

As indicated above, the multi-layer is especially construed by basically two-self terminating reactions. Different reactants may be chosen. However, in a specific embodiment sequentially compounds (II) and (III) are reacted:

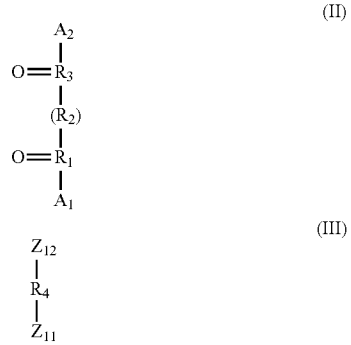

wherein R1, R2, R3, and R4 are independently selected from the group consisting of a carbon comprising group and a silicon comprising group, and wherein R2 may optionally be present wherein A1 and A2 are independently selected from OH and Cl, wherein Z11 and Z12 are each independently selected from an OH comprising group, an NH comprising group and an $NH_2$ comprising group. The compounds (II) and (III) are herein also indicated as (first and second) precursors or (first and second) reactants.

As indicated above, R2 may be present or may not be present. In the case R2 is present, formula II is indicated as:

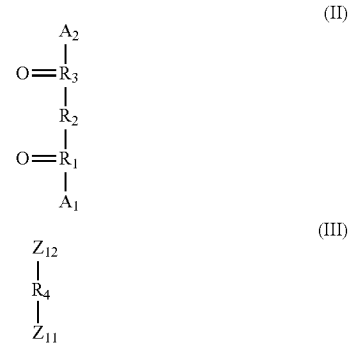

In other embodiments, R2 is not present, and formula II may be indicated as:

An example thereof is e.g. oxalic acid.

Not only two compounds can be applied in two self-terminating reactions, also three or more compounds can be used in (especially) three or more self-terminating reactions. Hence, in a further embodiment the invention provides a method wherein a number of times sequentially three compounds are reacted, and wherein the thus obtained molecular layer deposition (MLD) multi-layer comprises a stack of layers with each layer comprising the reaction product of the three compounds. Again, also hybrid constructions are possible.

In embodiments wherein sequentially compounds (II) and (III) are reaction, the compounds II and III may be identical for each reaction. However, in yet other embodiments, one or more of compounds II and III may differ between self termination reactions.

Further, the above indicated embodiment of a possible reaction is not intended to limit the invention. For instance, in a further embodiment one or more of the self-terminating reactions comprise a ring opening reaction.

As indicated above, specific examples thereof are malonyl chloride and 1,2-butanediol (see further also below).

However, in principle any, especially linear, acyl dichloride and in principle any, especially linear, diamine or diol might be applied.

Non-limiting examples of the former are malonyl chloride, butane dioyl dichloride, pentane dioyl dichloride, hexane dioyl dichloride, heptane dioyl dichloride, octane dioyl dichloride, nonane dioyl dichloride, decane dioyl dichloride, terephtaloyl dichloride, etc.; see also examples below.

Non-limiting examples of the latter are butane 1,4-diamine, pentane 1,5-diamine, hexane 1,6-diamine, heptane 1,7-diamine, octane 1,8-diamine, nonane 1,9-diamine, 1,10-diamine, butane 1,4-diol, pentane 1,5-diol, hexane 1,6-diol, heptane 1,7-diol, octane 1,8-diol, nonane 1,9-diol, decane 1,10-diol, etc.; see also examples below. Other non-limiting examples of the latter are butane 1,2-diamine, pentane 1,2-diamine, hexane 1,2-diamine, heptane 1,2-diamine, octane 1,2-diamine, nonane 1,2-diamine, decane 1,2-diamine, butane 1,2-diol, pentane 1,2-diol, hexane 1,2-diol, heptane 1,2-diol, octane 1,2-diol, nonane 1,2-diol, decane 1,2-diol, etc. Other distribution of the amine or hydroxyl group may also be possible, like butane 1,3-diamine, heptane 1,5-diol etc. etc.; see also examples below.

Instead of the acyl chlorides, also diacids may be applied. Hence, further non-limiting examples of one of the reactants may be selected from one or more of butane dicarboxylic acid, pentane dicarboxylic acid, hexane dicarboxylic acid, heptane dicarboxylic acid, octane dicarboxylic acid, nonane dicarboxylic acid, decane dicarboxylic acid, etc. For instance, examples may be selected from oxalic acid, malonic acid, succinic acid, glutaric acid, adipic acid, pimelic acid, suberic acid, azelaic acid, sebacic acid, brassilic acid. The groups R5 of the diester groups may be the same or may be different. Also molecules with different A1 and A2 groups may be selected. For instance, one end of molecule II may include an acyl chloride group and another end of molecule II may include an acid group. For instance, A1 may comprise OH and A2 may comprise Cl.

Here, diols or diamines, or acyl dichlorides or dicarboxylic acids, are described. However, also polyols or polyamines, or oligo acyl chlorides (or oligo acid chlorides), or oligo carboxylic acids ((or poly carboxylic acid) such as di carboxylic acid, tri carboxylic acid, etc.) may be applied. Hence, in an embodiment compound (II) is selected from an oligo carboxylic acid and an oligo acid chloride analogue, and wherein compound (III) is selected from a polyol and a polyamine.

Further, especially R1, R2, R3, and R4 do each independently not comprise more than twelve, especially not more than ten carbon atoms. When the chains get too long, the reactants may react with two functional groups at the surface, leading to a non-conformal layer. Hence, especially the total number of carbon (and silicon (when available)) atoms comprised by the molecules of compounds (II) and (III) are each independently especially not more than 12. Further, the total number of (silicon (when available) and) carbon atoms comprised by the compound (I) is especially not more than 24, such as not more than 18, like not more than 16, such as not more than 12, like at maximum 10.

In yet a further embodiment, A1 and A2 (of compound II) are independently selected from OH, Cl, OR5, and R6, such as especially from OH, Cl, and OR5.

Here, R5 is selected from the group consisting of a carbon comprising group and a silicon comprising group. Especially, R5 is a hydrocarbon group. In such embodiments, molecule comprises a polyester, especially a diester. Note that R5 is not necessarily the same for both A1 and A2. Further, A1 may be OH and A2 may be OR5, etc. Hence, A1 and A2 are not necessarily the same, though in embodiments they may be the same.

Further, especially the R5 group does not comprise more than twelve, especially not more than ten carbon atoms. When the chains get too long, the reactants may react with two functional groups at the surface, leading to an non-conformal layer. Hence, especially the total number of carbon (and silicon (when available)) atoms comprised by the molecules of compounds (II) and (III) are each independently especially not more than 12. Further, the total number of (silicon (when available) and) carbon atoms comprised by the compound (I) is especially not more than 24, such as not more than 18, like not more than 16, such as not more than 12, like at maximum 10.

Hence, in embodiments a diester, such as diethylsuccinate, may be used. Such diesters provide good coatings, with a similar release compared to the malonyl chloride formulation. An example of a precursors may include EtO—C(=O)—(CH2)n-C(=O)—OEt, whereby n=0-24. Other examples may include branched esters (having 2 ester groups, and >0 carbon chain groups) and branched esters (having >2 ester groups). In such embodiments, during the reaction ethanol (or another alcohol) may be formed, which is advantageous in view of reaction kinetics as well as in the situation where the formation of chlorinated compounds (as in the case of malonyl chloride) may not be desirable. This is schematically shown below:

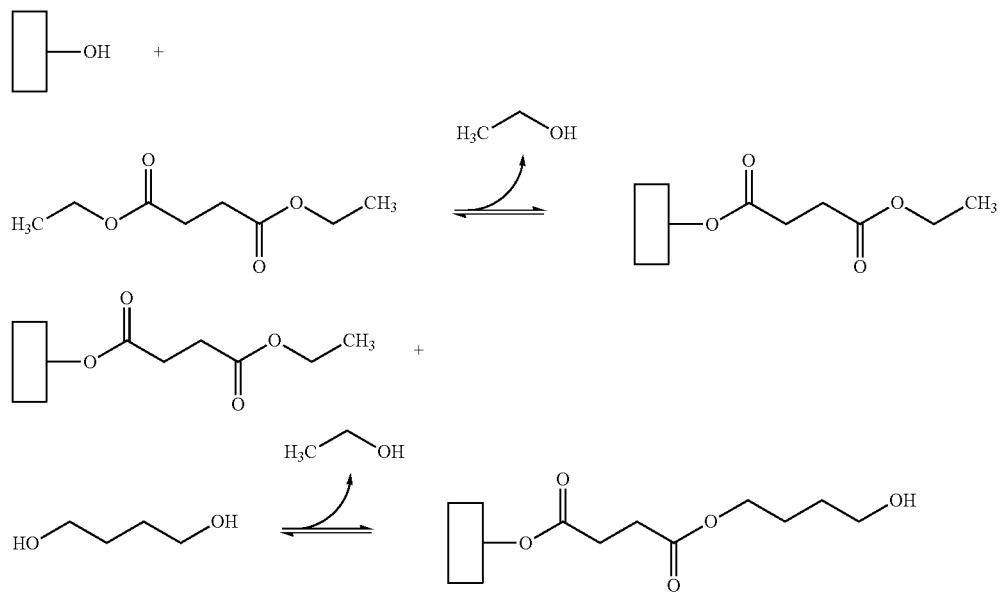

Here, the rectangle very schematically depicts a surface of the core, which may comprise OH groups.

R6 may refer to a triflate group, which is trifluoromethanesulfonate, also known by the trivial name triflate, which is a functional group with the formula $CF_3SO_3^-$. The triflate group is often represented by —Otf; $(S(CF_3)_3$—O—C$(=O)$—$(CH_2)_n$—C$(=O)$—O—$(CF_3)_3$ S). R6 may also refers to a mesylate group, which is a functional group with the formula $CH_3SO_3^-$; $(S(CH_3)_3$—O—C$(=O)$—$(CH_2)_n$—C$(=O)$—O—$(CH_3)_3$ S). Further, R6 may refer to a silyl ester; reactive $(Si(CH_3)_3$—O—C$(=O)$—$(CH_2)_n$—C$(=O)$—O—$(CH_3)_3Si)$. The indicator n in these formulas may be 0 or larger, such as in the range of 0-24, like 1-18, such as up to 12. R6 may be an easily removable group.

Further examples of precursors may include one or more of anhydrides, dioxane tetraketone (ring opening chemistry), etc.

Further examples of compound II are e.g. diesters of e.g. oxalic acid malonic acid, succinic acid, glutaric acid, adipic acid, pimelic acid, suberic acid, azelaic acid, sebacic acid, brassilic acid. The group(s) R5 of the diester groups may be the same or may be different.

With A1 and/or A2 being Cl or OH, esterification may take place; with A1 and/or A2 being OR5, transesterification may take place. In both cases, a catalyst may be applied (i.e. a catalyst is added in the gas phase). Especially, for trans-esterification it is good to add an exposure step for acid, for example hydrochloric acid or titanium tetrachloride, as this catalyzes the reaction between the ester and the diol. This catalyst may also be present in the core material prior to starting the coating process.

R1, R2, R3, R4, R5, can each independently comprise aliphatic hydrocarbons, aromatic hydrocarbons, polymeric chains, hydrocarbons comprising one or more ring structures. R1, R2, R3, R4, R5, can each independently be branched or unbranched. Especially, R2 and R4 may each independently be linear or cyclic. In an embodiment, one or more of R1, R2, R3, R4, R5, are unbranched. Especially, in embodiments any of R1, R2, R3, R4, R5, available is unbranched.

Non-limiting examples of precursors are indicated in the table below:

Here, the term "start-end" indicates that the functional groups are at the head and terminal position of the hydrocarbon chain. The term "start-next" that the functional groups are next to each other. For the sake of ease, the precursors C5-C9 have not been listed with there names, but they are also possible as precursors. Especially, C2-C10 are the interesting precursors. Their chemical formulas can be derived from the table, as the number of carbon atoms, the type of functional groups, as well as "start-end" or "start-next" is indicated.

As indicated above, in a specific embodiment the core (i.e. the particle provided to the reactor to be coated with the MLD process) comprises a diameter (d1) selected from the range of 1 nm-2 mm. The method as described herein may further comprise applying molecular multi-layer deposition until a multi-layer shell of 2-1000, such as 2-500, like 2-100 layers is obtained. With the method described herein the particles as described herein may be obtained. Hence, in a specific embodiment the (particulate) material as defined herein is obtainable with the method as described herein.

The material thus obtained, which is thus especially a particulate material, comprises particles as defined above. Note that the term particulate material does not exclude that the material comprises aggregates of particles. Especially, however, the material is (still) a particulate material comprising particles (and optionally also agglomerates of particles). The thus obtained material may be further processed, e.g. to provide a suspension, to provide a solution, to provide granules, etc. Further, after the molecular multi-layer deposition optionally further layers may be applied, e.g. with other processes like sol-gel, CVD, etc. In this way the outer layer may further be functionalized for application (e.g. in the human body, in a suspension, etc.). Of course, it may also be possible to use the molecular multi-layer deposition itself to create a specific outer layer, different from the other layers of the MLD multi-layer. Hence, the method of the invention may further include a subsequent processing of the (particulate) slow release material.

In yet further embodiments the invention thus also provides the slow release material as a solution, a powder, a granulate, a tablet, a suspension, etc., comprising said slow-release particles. For instance, though e.g. for gastro intes-

|  | dichloride start-end | diamine start-end | diamine start-next | diol start-end | diol start-next | diacid start-end |
|---|---|---|---|---|---|---|
| aliphatic | | | | | | |
| C2 | oxalyl chloride | ethylene-diamine | ethylene-diamine | ethylene glycol | ethylene glycol | oxalic acid |
| C3 | malonyl chloride | 1,3-propane diamine | 1,2-propane diamine | 1,3-propanediol | 1,2-propanediol | malonic acid |
| C4 | succinyl chloride | 1,4-butane diamine | 1,2-propane diamine | 1,4-butanediol | 1,2-butane-diol | succinic acid |
| C5 | Etc. | Etc. | Etc. | Etc. | Etc. | Etc. |
| C6 | | | | | | |
| C7 | | | | | | |
| C8 | | | | | | |
| C9 | | | | | | |
| C10 | sebacoyl chloride | 1,10-decane diamine | 1,2-decane diamine | 1,10-decanediol | 1,2-decanediol | sebacic acid |
| aromatic | | | | | | |
| C6 | | p-phenylene diamine | o-phenylene diamine | hydroquinone | catechol | |
| C8 | terephthaloyl chloride | | | | | terephthalic acid | tinal applications the particle size may be in the range of e.g. 0.01-2 mm, still tablets may be used that substantially (first) disintegrate into these particles (of e.g. 0.01-2 mm). Hence, the invention also provides a medicament comprising the particulate slow-release material as defined herein, and especially obtainable with the method as described herein, especially for use in the treatment of a disease. In a specific embodiment, the slow-release material, or e.g. a medicament comprising the slow-release material is especially to be administered orally. In such applications, the invention may especially be beneficial.

In yet a further embodiment, the slow-release material may comprise particles having different properties. In an embodiment, there are two or more subsets of particles, wherein the particles of the subsets comprise different active components, respectively. In yet another embodiment, there are two or more subsets of particles, wherein the particles of the subsets comprise different multi-layer shell thicknesses and/or different compositions of the multi-layer shell, respectively. These embodiments may e.g. be applied to further control release of the active component, for instance at a specific part of the GI tract and/or upon exposure to different pH environments in the GI tract, etc. Hence, in these ways release profiles may be defined. Therefore, the invention also provides a slow-release material having a trigger and/or time controlled release. The term "slow release" encompasses both a time controlled release and a trigger controlled release, as is known in the art. The term "slow release" is known in the art and especially refers to embodiments wherein a compound is introduced into a system, such as a human, at a reduced speed. Hence, the compound is especially not dosed at once into the system but is released over time, such as over at least 5 minutes, even more especially at least 20 minutes, even more especially at least 60 minutes, such as over a period in the range of 5 minutes to 48 hours, like 60 minutes to 24 hours, such as to 12 hours.

Hence, in yet further embodiments the method may further comprise one or more of (i) providing an additional coating, (ii) producing a dosage form comprising the slow-release material, and (iii) packaging the slow-release material or dosage form, respectively. Packaging may especially be a last stage in the method for the production of the slow-release material. Packaging may be preceded by producing a dosage form. Producing a dosage form may optionally be preceded by providing an additional coating. Such coating may e.g. comprise a colorant. Further, such coating may especially be provided with another process than MLD. In yet further embodiments, the additional coating may be provided after having produces a solid dosage form, such as a tablet (with thus the tablet being coated). Examples of dosage forms include pills, tablets, capsules, drinks or syrups. Especially, the dosage form may be solid, such as a pill, tablet or capsule.

Hence, the invention provides in embodiments a molecular layer deposition process for providing a layer of an organic polymer or organic-inorganic polymer, especially organic polymer, onto a substrate, wherein the method comprises contacting the core (and subsequently the layer(s) formed therein) sequentially and alternatingly with a first reactant and a second reactant to provide a polymer, wherein especially the first reactant reacts especially mono functionally with a secondary functional group on the polymer to form a bond to the polymer and to provide a primary functional group on the polymer (thus obtained), and wherein the second reactant also reacts especially mono functionally with the primary functional group to form a bond to the polymer and to provide a (further) secondary functional group on the polymer chain, wherein the polymer may thus especially be an organic polymer or an organic-inorganic polymer, even more especially on organic polymer. The term "polymer" may also refer to a block copolymer.

Especially, the invention provides particles, wherein the particles comprise a core, especially comprising an active component, and a plurality of molecules attached to the core, thereby forming a shell around the core, wherein the active component may especially comprises one or more components selected from the group of a pharmaceutical compound and a nutraceutical compound, especially (a pharmaceutical compound, even more especially a drug), such as for use in the treatment of a disease, and wherein the molecules of the plurality of molecules especially comprise at least two groups I as described herein, such as 2-1000 of such groups. Hence, polymers may be attached to the core, forming a multi-layer shell, as substantially all the polymers may all have identical groups I. In specific embodiments, all groups I are identical (when only two types of precursors is applied). In other embodiments, more than two types of precursors may be applied, which may lead to block copolymers.

Hence, the invention also provides in an aspect a core-shell particle, comprising a core comprising an active component and a shell, wherein especially the active component comprises one or more of a pharmaceutical compound and a nutraceutical compound, wherein the shell comprises a plurality of polymers, with each polymer attached with one end to the core, and each polymer comprises one or more groups defined by formula (I), especially a plurality of groups defined by formula (I):

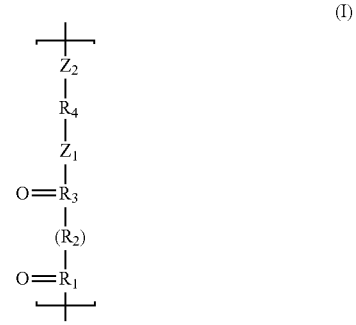

wherein R1, R2, R3, and R4 are independently selected from the group consisting of a carbon comprising group, wherein Z1 and Z2 are each independently selected from an oxygen or nitrogen comprising group, and wherein R2 is optionally present. Such particle may be available via MLD, especially via fluidized bed MLD.

In yet a further embodiment, the invention also provides a reactor for fluidizing particles comprising a (particle) diameter selected from the range of 1 nm-2 mm (here the diameter especially refers to the cores), wherein the reactor comprises a first inlet for introduction of one or more reactants in the gas phase, wherein the reactor further optionally comprises a vibration generator configured to subject the reactor to a vibration having a frequency selected from the range of 1-200 Hz, and wherein the reactor further optionally comprises a second inlet for a gas, configured to provide during operation a counter flow relative to a flow introduced in the reactor via the first inlet. This reactor may especially be applied for executing the method as described herein. Hence, the method of the invention may also include using the reactor as defined herein. Especially, the invention provides an apparatus comprising such reactor, wherein the apparatus may be configured to execute the herein described method.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 1a-1d provide illustrations of the reactions involved in an MLD process;

Figure 1C:
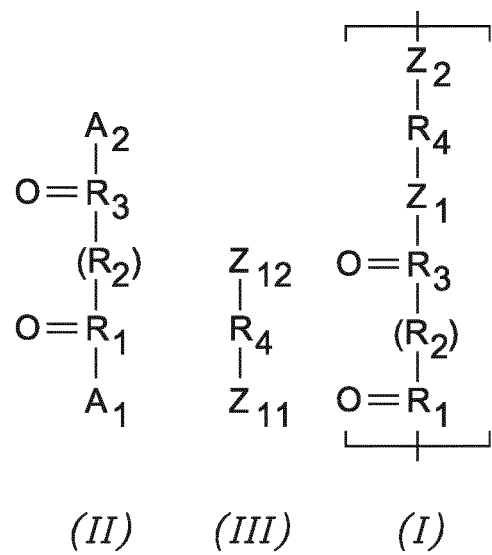

The schematic drawings are not necessarily on scale.

DETAILED DESCRIPTION OF THE EMBODIMENTS

To demonstrate the concept, we used protein particles as the substrate and the precursors used are malonyl chloride and 1,2-butanediol. An illustration of the reactions involved is shown in FIG. 1a. References RE1-RE3 refer to reactions 1-3. Note that reaction 3 is the same as reaction 1, hence, with reaction 3 and (further reaction analogous to reaction two) a second layer may be formed. Reference 100 indicates a particle and reference 110 indicates a core. The particle, yet without multi-layer layer, i.e. in fact the core 110, has a surface 111. Reference 121 indicates a layer (which is formed by the two self-terminating reactions; reference 121a indicates the first layer, which is covalently linked to the surface 111. The basic compound formed, here an ester, is indicated with reference (I). By way of example, amine groups are shown at the surface 111 of the bare particle 100. As can further also be seen in FIG. 1b, the two self-terminating reactions include a first reactant and a second reactant (embodiments thereof are herein also indicated as compounds (II) and (III), which after the two self-terminating reactions lead to a monolayer 121. The parts of the monolayer originating to these two reactants are in FIG. 1a indicated as A and B. RE1 and RE3 may thus essentially be the same reactions.

More in general, the elementary reactions that can be involved are indicated in FIG. 1b. The amine group on the surface of the protein particles acts as the active group for reaction with the acyl chloride group of malonyl chloride during the first reaction step. In the second reaction step, the unreacted acyl chloride group of malonyl chloride which is now attached to the surface of the substrate acts as the active site for the reaction with the hydroxyl group of 1,2-butanediol. In the third reaction step, the unreacted hydroxyl group of 1,2-butanediol reacts with the acyl chloride group of malonyl chloride.

Figure 1D:
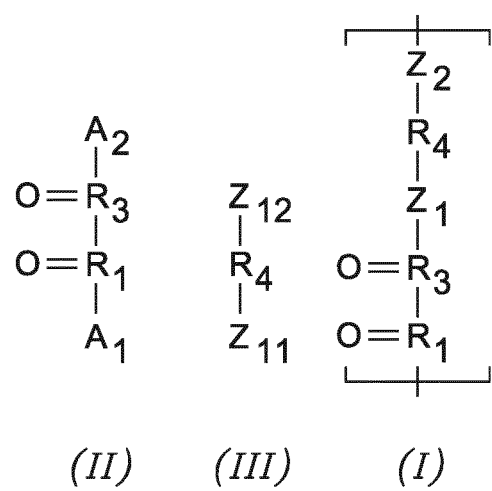

FIG. 1b schematically depicted the two compounds II and III which may result in chains including group I after a reaction of compounds II and III. In these formulas, R2 may be available. However, R2 is not necessarily available. This is indicated in FIG. 1c. When R2 is not available, the formulas as indicated in FIG. 1d may be applied.

Only the first coating cycle involves reaction step one and two, while subsequent coating cycles involves reaction step three and two. Each cycle generates a single layer. Note that the numbering is only used to differentiate between reactions. Hence, step three and two may herein also be indicated as a first self-terminating reaction and a second self-terminating reaction.

Figure 2:
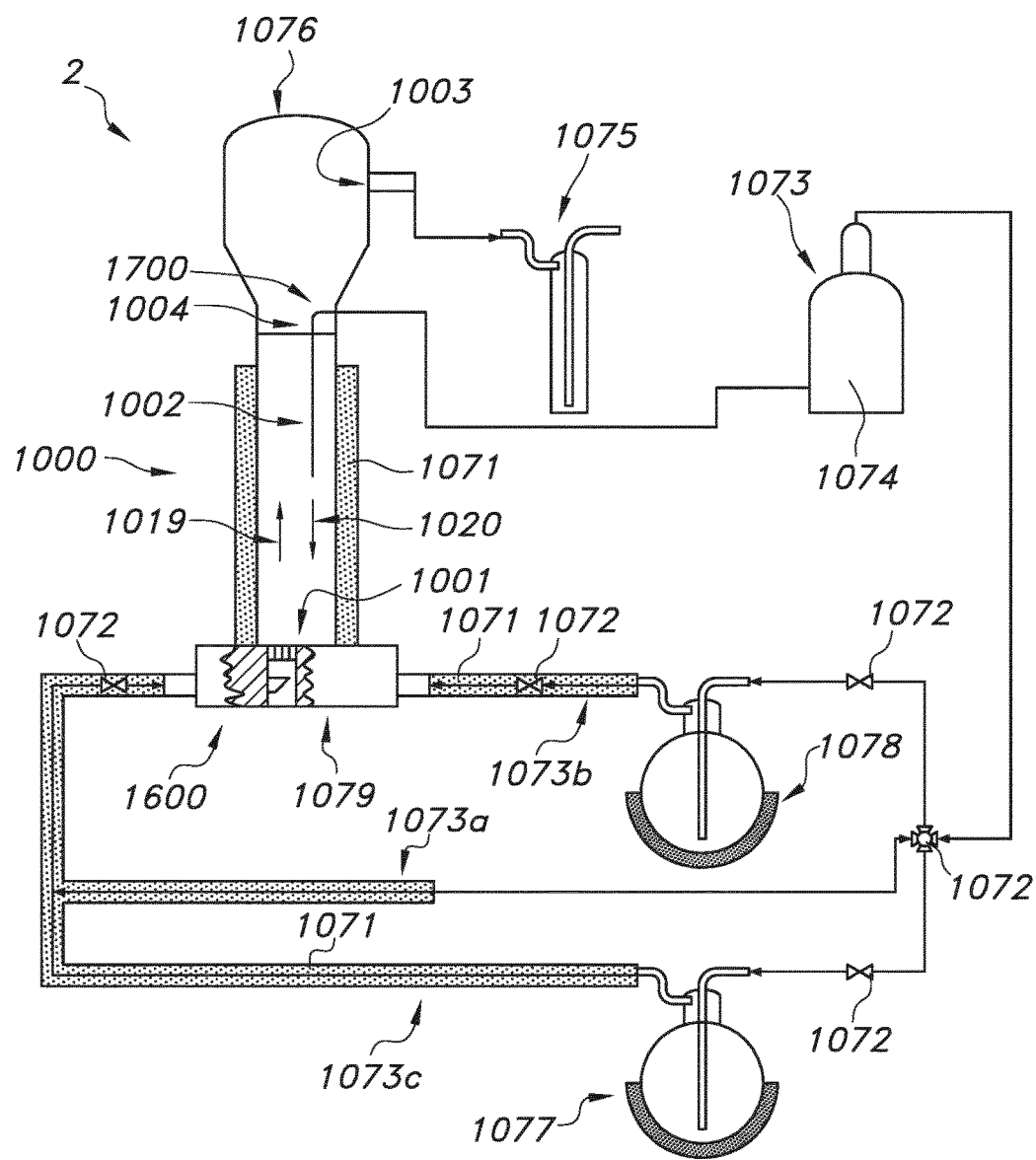
FIG. 2 provides a schematic diagram of the experimental setup used for the MLD process.

In an experiment, 2 g of protein particles with an average diameter of 200 µm is suspended in an upward gas flow of pure $N_2$, this is called a fluidized bed. $N_2$ acts as the carrier gas for feeding the precursors into the fluidized bed reactor (FBR). A schematic diagram of the experimental setup is shown in FIG. 2. The reactor or fluidized bed reactor is indicated with reference 1000.

The FBR primarily consists of a vertical glass tube with an inner diameter of 2.6 cm and length of 40 cm with thermocouples inserted at the entrance and exit. The FBR is maintained at a temperature between 40° C. and 45° C. using an infrared lamp. It may be desired to maintain considerably low temperatures because the protein used is found to denature at a temperature above 55° C. The denaturation temperature of the protein to a great extent limited the choice of precursors for the MLD process. Due to the low vapor pressures of malonyl chloride and 1,2-butanediol, respectively, at room temperature they are preheated to 40° C. and 115° C. in bubblers 1077,1078, respectively. A distributor plate 1079 is provided at the entrance or inlet 1001 of the FBR to ensure uniform distribution of the inlet gas stream mixture. By measuring the particle bed height variation with flow rate, the minimum velocity required to keep the particles afloat in $N_2$ gas is determined to be $2.7 \times 10^2$ ms$^{-1}$. This velocity is often referred to as the minimum fluidization velocity. The unreacted precursor and by-product of the reaction HCl is trapped using a mineral oil cold trap 1075 at the exit or outlet 1003 of the FBR. We employ two methods to improve the fluidization of the particles: mechanical vibration of the FBR at a frequency of 50 Hz, and a microjet 1004 of 100 µm. The microjet is inserted into the FBR from the top and the mechanical vibrator is fixed at the bottom of it. The microjet ensures good fluidization by breaking the agglomerates formed during the coating process. Reference 1700 indicates the microjet unit, further comprising a gas flow generator 1073, with gas 1074, such as $N_2$. Reference 1002 indicates the outlet or nozzle of the microjet 1004. Reference 1600 indicates the vibration generator. References 1072 indicate valves. References 1071 indicate a heating system. Reference 1076 indicates an expansion of the column diameter to reduce the outflow of particles. Reference 2 indicates an MLD apparatus, comprising the reactor 1000 and further elements, including optional items such as the microjet unit 1700 and the vibration generator 1600, to execute the method as defined herein. Here, by way of example the gas flow generator 1073 is used for the microjet unit 1700 and the gas flow for generating the fluidized bed. Of course, this can be two or more (independent) gas flow generators.

Particles coated to different number of cycles are prepared. A typical coating cycle consists of four steps: 30 s dosage of malonyl chloride; minimum 2 min of purging with pure $N_2$ to remove the unreacted precursor; 30 s dosage of 1,2-butanediol and finally purging with pure $N_2$ for at least 2 min. We observed a tendency for particle agglomeration during the reaction steps in a coating cycle which aggravates with increase in number of cycles. This increased agglomeration affects the fluidization of the particles and in certain cases the fluidization is completely lost. Purging the FBR with high flow rate $N_2$ gas for long duration of time reinforced fluidization. Hence, for later cycles the reactor was purged until the fluidization was completely re-established. Particles were coated with 2, 6 and 10 MLD cycles. In this embodiment, by way of example three gas transport lines 1073a-1073c are depicted, for providing gas to provide a fluidized bad (gas transport line 1073a), to provide a first reactant (gas transport line 1073b), and to provide a second reactant (gas transport line 1073c). Reference 1019 indicates the direction of the gas flow in the fluidized bed reactor. The microjet unit 1700 may provide a counter flow 1020.

Fourier transform infrared (FTIR) spectroscopy has been used to characterize the coating of protein particles. FTIR spectra are obtained using a Nicolet 8700 FTIR spectrometer (Thermo Electron Corporation) operating with a liquid $N_2$ cooled KBr/DLaTGS D301 detector. FTIR spectra of the coated protein particles are obtained by pressing the sample onto KBr salts and the data is collected with a resolution of 4 cm$^{-1}$ averaged over 128 scans. The FTIR spectra of the coated particles shown in FIG. 3 are subtracted results from the spectra of the uncoated particles.

Figure 3:
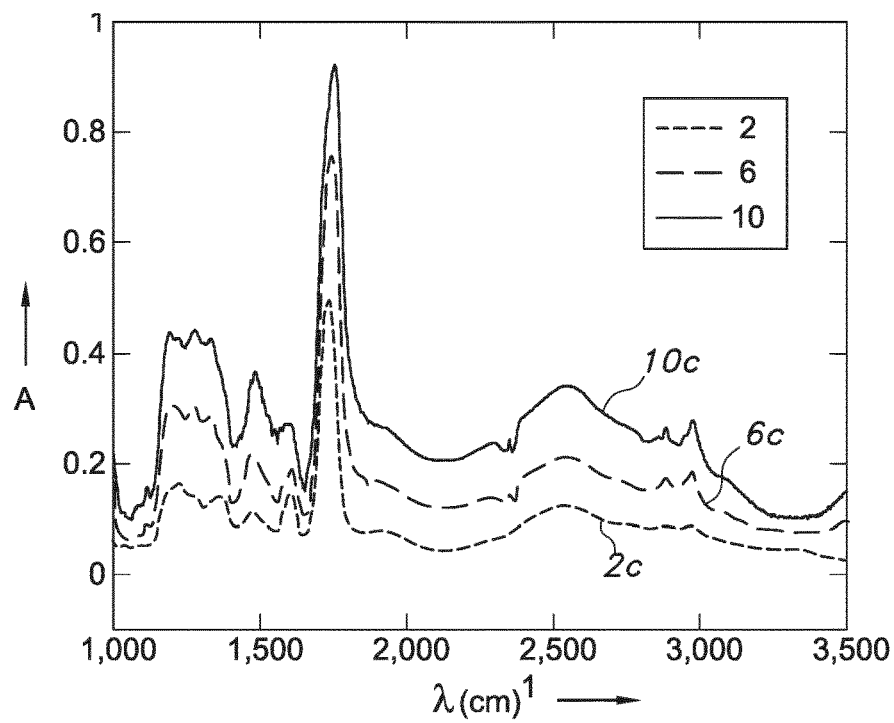
FIG. 3 provides FTIR spectra (absorption (A) vs. wavenumber (in cm$^{-1}$)) for 2, 6 and 10 cycles sample.

In FIG. 3, three distinct peaks are observed very close to 1480 cm$^{-1}$, 1736 cm$^{-1}$ and 2971 cm$^{-1}$, these correspond respectively to the stretching of [—CH$_2$—],[—COO—] and [CH$_3$—] groups. Increase in the absorbance peak due to [—COO—] and [CH$_3$—] stretching indicates the increase in coating thickness with number of cycles. In FIG. 3, the x-axis indicates the wavenumber in cm$^{-1}$, and the y-axis indicates the absorbance (in arbitrary units). References 2C, 6C, and 10C indicates the number of cycles, being respectively 2, 6, and 10.

Dissolution experiments have been performed to study the controlled release of the coated protein samples. All the dissolution experiments have been performed at room temperature and atmospheric pressure. 0.15 g of a coated particle sample is dissolved in 150 ml of deionized water. The resulting mixture was stirred with a magnetic stirrer to ensure uniform dispersion of the particles in deionized water. However, due to their low density most of the coated particles remain on the surface of the solution. Samples have been collected at regular intervals for a time period of 30 min. The collected samples are immediately filtered through a 0.45 µm pore size polyvinylidene difluoride membrane (MillexOR) to avoid further dissolution of protein particles. After a time period of 30 min, undissolved protein particles denatured to form strands in the solution.

UV-vis spectroscopic measurements (UV-1800, Shimadzu) were performed on the collected dissolution experiment samples of uncoated and coated protein particles at a wavelength of 260 nm. The results are shown in FIG. 4.

Figure 4:
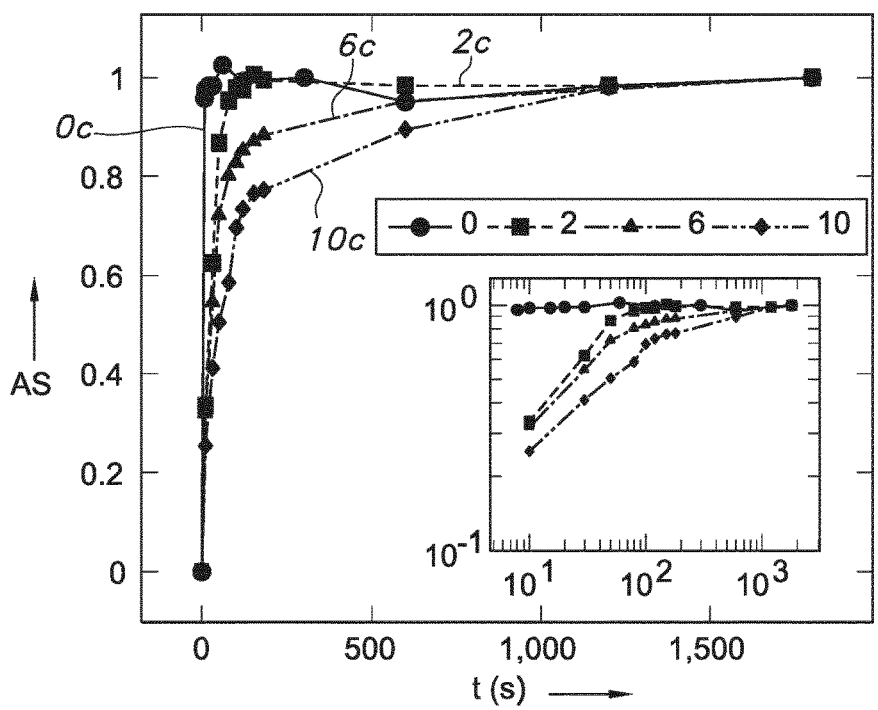
FIG. 4 provides an UV-vis absorbance (AS) versus time (seconds) test result for protein particles coated with different numbers of cycles.

In FIG. 4, AS indicates the scaled absorbance is defined as $(A(t)-A(t=0))/(A(t=1800 \text{ s})-A(t=0))$, where $A(t)$ is the absorbance at time t and $A(t=0)$ is assumed to be zero. Here, scaled absorbance gives a measure of scaled concentration because absorbance scales linearly with concentration. The solution containing uncoated sample attains maximum concentration in about 10 s, while the coated samples dissolve at a much slower rate. In the inset of FIG. 4, the UV-vis test results are plotted on a log-log scale. Two distinct regions are observed: initial short time scale ~30 s corresponding to a fast release of the coated protein and the long time scale ~1000 s corresponding to a slow release of the coated protein. References 0C, 2C, 6C, and 10C indicates the number of cycles, being respectively 0, 2, 6, and 10. The x-axis indicates the time (in seconds).

The fast and slow regions are fitted individually to a power law function which scales with time as $t^\alpha$. The values of $\alpha_{fast}$ for 2, 6 and 10 cycles sample, are respectively 0.482±0.166, 0.425±0.121 and 0.422±0.059. $\alpha_{fast}$ values obtained are close to 0.5 which is observed in diffusion governed dissolution mechanism models. We suspect the close resemblance of the fast release exponent to that of diffusion governed drug release mechanism models could be due to the presence of protein particles whose surface area is not completely coated. These particles are formed as a result of continuous breakage and formation of agglomerates, respectively, during purging and precursor dosage periods. For the 2 cycles sample, $\alpha_{slow} \sim 0$ indicating that the maximum concentration has been attained after a time period of 100 s. However, for 6 and 10 cycles sample, respectively, $\alpha_{slow}$ is found to be 0.058±0.008 and 0.117±0.013.

In conclusion, we found that with increase in coating cycles of MLD the thickness of coating increases as shown by FTIR. We also demonstrate experimentally that controlled release of protein particles can be realized by MLD. The controlled-release behavior is validated through dissolution experiment of coated particles wherein the decrease in the rate of dissolution is observed with increase in the number of coating cycles.

This proof-of-principle demonstrates that MLD of fluidized particles is an attractive way to give protein materials tunable controlled-release properties.

Figure 5A:
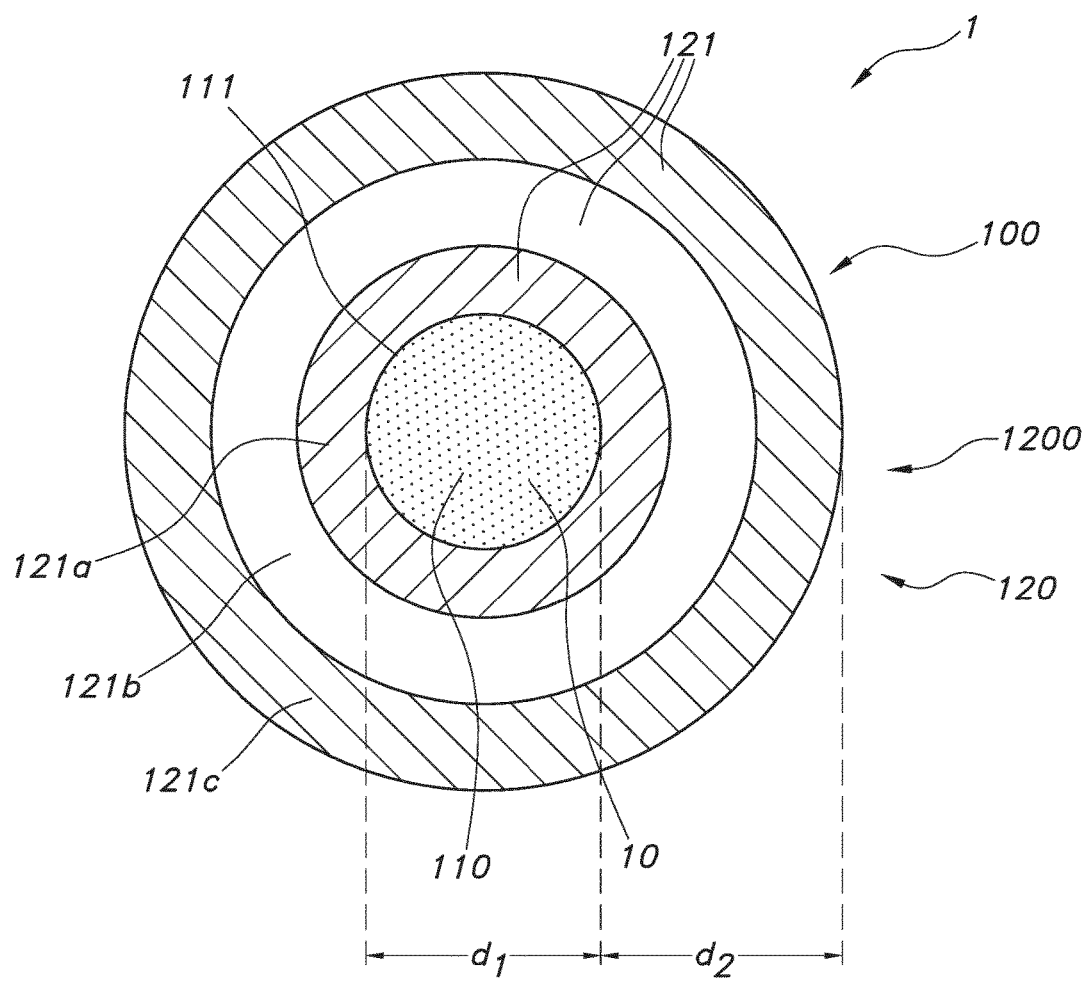
FIGS. 5a-5b schematically depict some aspects of the invention.

FIG. 5a schematically shows the (particulate) slow-release material 1, here by way of example only schematically indicated with a single particle 100, wherein the particle 100 comprise a core 110 comprising an active component 10 and a multi-layer shell 120. The multi-layer shell 120 comprises a molecular layer deposition MLD multi-layer 1200. As indicated above, especially the active component comprises one or more of a pharmaceutical compound and a nutraceutical compound, such as for use in the treatment of a disease. The core 110 comprises a diameter d1, such as selected from the range of 1 nm-2 mm. The multi-layer shell 120, especially the molecular layer deposition multi-layer 1200 comprises a layer thickness d2 selected from the range of 2-1000 layers 121. The layers are herein indicated with references 121a, 121b, etc.

Figure 5B:
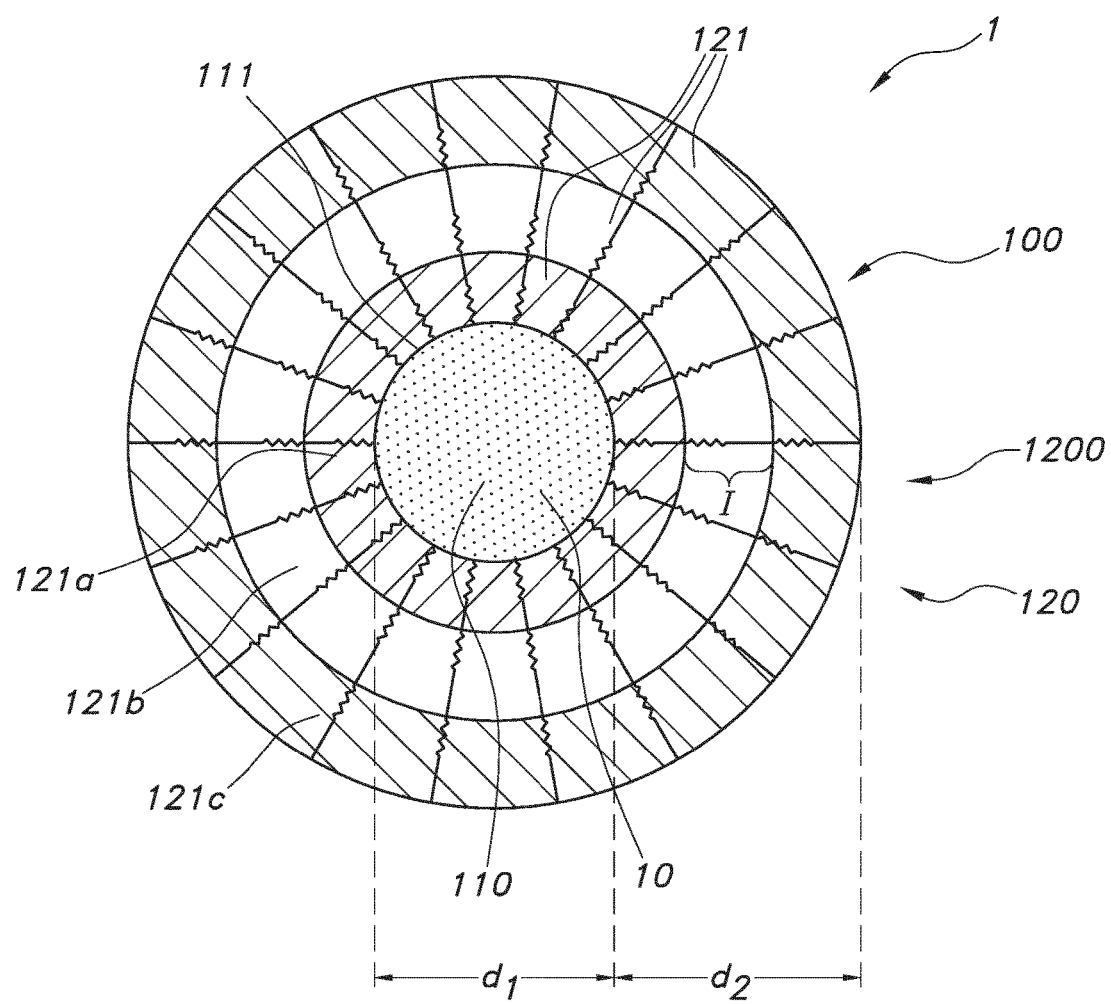

Small polymer chains (oligomers when there are two layers) are in this way grown to the surface of the core 10. This may lead to a kind of spaghetti configuration of polymers to the surface, with units I available in one or more, or substantially all chains. Step by step these chains are formed in a molecular layer deposition process leading to layer formation, which layers are provided by the groups I. This is schematically shown in FIG. 5b. Therefore, in embodiments the invention provides core-shell particles, wherein the shell is provided by a plurality of polymer chains, each (chemically) attached with one end to core, and each polymer comprising a one or more, especially a plurality, of groups I.

A further MLD coating was formed by exposing dried powders (containing an active ingredient) alternatively to diethyl succinate and 1,4-butanediol. The precursors were contained in 100 mL glass round bottom flasks heated at respectively 80-95° C. and 100-125° C. by heating mantles. Precursors were transported in a nitrogen flow (0.4 L/min). The tube lines heading to the column were heated by heating tapes to prevent precursor condensation. Presence of MLD coating was confirmed by delayed release of active ingredient.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A slow-release material (1) comprising particles (100), wherein the particles (100) comprise a core (110) comprising an active component (10) and a multi-layer shell (120), wherein the multi-layer shell (120) comprises a molecular layer deposition (MLD) multi-layer (1200), wherein the active component comprises one or more of a pharmaceutical compound and a nutraceutical compound, for use in the treatment of a disease, and wherein each layer (121) of the multi-layer shell (120) comprises a group defined by formula (I):

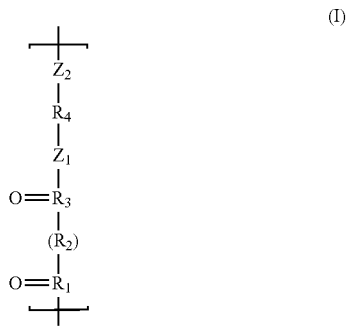

wherein R1, R2, R3, and R4 are independently selected from the group consisting of a carbon comprising group, wherein Z1 and Z2 are each independently selected from an oxygen or nitrogen comprising group, and wherein R2 is optionally present.

2. The slow-release material (1) according to claim 1, wherein the core (110) comprises a diameter (d1) selected from the range of 1 nm - 2 mm, and wherein the multi-layer shell (120) comprises in the range of 2-1000 layers (121).

3. The slow-release material (1) according to claim 1, wherein a first molecular layer (121a) is covalently linked to a surface (111) of the core (110).

4. The slow-release material (1) according to claim 3, wherein R1=R3=C, R2=CH$_2$, R4=-(CH$_2$)C(CH$_2$CH$_3$)—, and Z1=Z2=O.

5. The slow-release material (1) according to claim 1, wherein the active component (10) comprises a pharmaceutical compound, and wherein the core further comprises a pharmaceutically acceptable carrier and/or a pharmaceutically acceptable filler.

6. The slow-release material (1) according to claim 1, wherein the active component (10) comprised by said core (110) has an active component solubility in water, wherein the multi-layer shell (120) has a multi-layer shell solubility in water, wherein the multi-layer shell solubility is smaller than the active component solubility.

7. A core-shell particle (100), comprising a core (110) comprising an active component (10) and a shell (120), wherein the shell (120) comprises a plurality of polymers, with each polymer attached with one end to the core, and each polymer comprises a plurality of groups defined by formula (I):

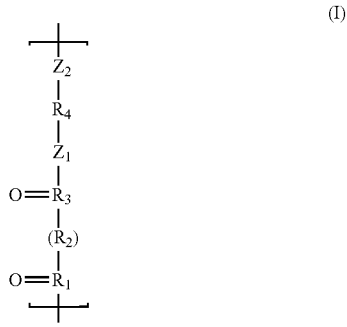

wherein R1, R2, R3, and R4 are independently selected from the group consisting of a carbon comprising group, wherein Z1 and Z2 are each independently selected from an oxygen or nitrogen comprising group, and wherein R2 is optionally present.

8. A method for the production of a slow-release material (1) according to claim 1, the method comprising:
fluidizing particles (100) comprising an active component (10) in a reactor (1000), wherein the active component comprises one or more of a pharmaceutical compound and a nutraceutical compound;
applying molecular multi-layer deposition with self-terminating reactions on said fluidized particles (100) in said reactor (1000), wherein sequentially compounds (II) and (III) are reacted:

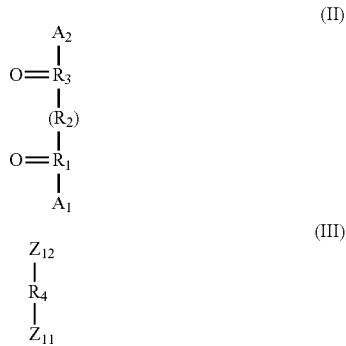

wherein R1, R2, R3, and R4 are independently selected from the group consisting of a carbon comprising group, wherein R2 is optionally present, wherein A1 and A2 are independently selected from OH, Cl, and —OR5, wherein R5 is selected from the group consisting of a carbon comprising group and a silicon comprising group, wherein Z11 and Z12 are each independently selected from an OH comprising group, an NH comprising group and an $NH_2$ comprising group;
removing the thus obtained particles from said reactor (1000), to provide said slow-release material (1).

9. The method according to claim 8, wherein during the molecular multi-layer deposition the reactor (1000) is subjected to a vibration having a frequency selected from the range of 1-200 Hz.

10. The method according to claim 8, wherein the reactor has a top part (1076), wherein the method further includes providing a counter flow (1020) from the top part (1076) into the reactor (1000).

11. The method according to claim 10, wherein the counter flow (1020) is provided into the reactor (1000) via a micro jet (1004).

12. The method according to claim 8, wherein the molecular multi-layer deposition is executed at a temperature selected from the range of 35-150° C. and at a pressure selected from the range of 0.8-2 bar.

13. The method according to claim 8, wherein the particles (100) comprise a surface (111) comprising amine groups.

14. The method according to claim 8, wherein a number of times sequentially three compounds are reacted, and wherein the thus obtained molecular layer deposition (MLD) multi-layer (1200) comprises a stack of layers (121) with each layer (121) comprising the reaction product of the three compounds.

15. The method according to claim 8, wherein one or more of the self-terminating reactions comprise a ring opening reaction.

16. The method according to claim 8, wherein compound (II) is selected from an oligo carboxylic acid and an oligo acid chloride analogue, and wherein compound (III) is selected from a polyol and a polyamine.

17. The method according to claim 8, wherein the core (110) comprises a diameter (d1) selected from the range of 1 nm-2 mm, and wherein the method comprises applying molecular multi-layer deposition until a multi-layer shell (120) of 2-100 layers (121) is obtained.

18. The method according to claim 8, further comprising one or more of providing an additional coating, producing a dosage form comprising the slow-release material (1), and packaging the slow-release material (1) or dosage form, respectively.

19. The method according to claim 8, wherein the method comprises depositing a molecular layer deposition (MLD) multi-layer (1200) onto particles being pneumatically transported in a tube, said process comprising: (i) providing a tube having an inlet opening and an outlet opening; (ii) feeding a carrier gas entraining particles into the tube at or near the inlet opening of the tube to create a particle flow through the tube; (iii) injecting a first reactant into the tube via an injection point downstream from the inlet opening of the tube for deposition on the surface of the particles in the particle flow in a self-terminating reaction; and (iv) injecting a second reactant into the tube via a further injection point downstream from the injection point of the first reactant for deposition on the surface of the particles in the particle flow in a self-terminating reaction.

20. A reactor (1000) for producing the slow-release material according to claim 1, wherein said reactor fluidizes said particles (110) comprising a diameter (d1) selected from the range of 1 nm - 2 mm, wherein the reactor (1000) comprises a first inlet (1001) for introduction of one or more reactants in the gas phase, wherein the reactor (1000) further comprises a vibration generator (1600) configured to subject the reactor (1000) to a vibration having a frequency selected from the range of 1-200 Hz, wherein the reactor (1000) further comprises a second inlet (1002) for a gas, configured to provide during operation a counter flow relative to a flow introduced in the reactor (1000) via the first inlet (1001).

* * * * *